United States Patent [19]

Knifton

[11] 4,451,680
[45] * May 29, 1984

[54] ALCOHOLS PREPARED FROM OLEFINS AND SYNTHESIS GAS

[75] Inventor: John F. Knifton, Austin, Tex.

[73] Assignee: Texaco Inc., White Plains, N.Y.

[*] Notice: The portion of the term of this patent subsequent to May 29, 2001 has been disclaimed.

[21] Appl. No.: 435,813

[22] Filed: Oct. 21, 1982

[51] Int. Cl.$^3$ .............................................. C07C 27/22
[52] U.S. Cl. .................................. 568/909; 568/451; 568/454
[58] Field of Search ...................... 568/451, 454, 909

[56] References Cited

U.S. PATENT DOCUMENTS

| | | | |
|---|---|---|---|
| 3,527,809 | 9/1970 | Pruett | 568/454 |
| 3,636,159 | 1/1972 | Solomom | 568/454 |
| 4,306,084 | 12/1981 | Pettit | 568/454 |
| 4,306,085 | 12/1981 | Kim et al. | 568/454 |
| 4,317,936 | 3/1982 | Kim et al. | 568/454 |

FOREIGN PATENT DOCUMENTS

| | | | |
|---|---|---|---|
| 751353 | 12/1970 | Belgium | 568/454 |
| 988943 | 7/1961 | United Kingdom | 568/454 |
| 966482 | 8/1964 | United Kingdom | 568/454 |
| 999461 | 7/1965 | United Kingdom | 568/909 |

OTHER PUBLICATIONS

Suss-Fink "J. Organomet. Chem" 193 C20-22 (1980).
Pittman et al "J. Org. Chem." vol. 46, p. 1901 (1980).
Wilkinson et al "J. Chem. Soc." Dalton, p. 399+ (1976).

*Primary Examiner*—Werren B. Lone
*Attorney, Agent, or Firm*—Robert A. Kulason; Jack H. Park; Cynthia L. Kendrick

[57] ABSTRACT

This invention concerns a process of preparing predominantly linear alcohols which comprises the steps of contacting a mixture of terminal and/or internal olefins and synthesis gas with a catalyst system comprising a ruthenium-containing compound coupled with one or more bidentate or multidentate, phosphine-containing promoters, dispersed in a low melting quaternary phosphonium salt, and heating said resultant reaction mixture under a pressure of 100 psi or greater at a temperature of at least 50° C. for a sufficient time to produce said alcohols.

23 Claims, No Drawings

ALCOHOLS PREPARED FROM OLEFINS AND SYNTHESIS GAS

BACKGROUND OF THE INVENTION

1. Field of the Invention

This invention concerns an improved process for preparing predominantly linear alcohols by the reaction of synthesis gas and terminal or internal olefins in the presence of a catalyst system.

2. Prior Art

The processes of hydroformylation and carbonylation are well known in the art and involve reactions represented by:

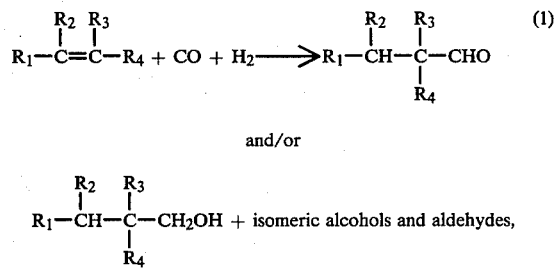

and/or $$R_1-CH-\underset{\underset{R_4}{|}}{\overset{\overset{R_3}{|}}{C}}-CH_2OH + \text{isomeric alcohols and aldehydes,}$$

wherein the aldehydes and alcohols produced by the reaction of olefinic compounds with carbon monoxide and hydrogen generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with consequent variation in the products obtained.

The hydroformylation reaction does not generally proceed in the absence of catalysts, and a disadvantage of many of the hydroformylation processes disclosed heretofore is their dependence upon the use of catalysts, particularly the commonly used cobalt-derived homogenous 'oxo' catalysts, which generally necessitate the use of exceedingly high pressure to remain stable under the conditions employed. A further disadvantage of many of the processes disclosed heretofore is their inability to produce hydroformylation products comprising substantial amounts of alcohols, thereby necessitating a separate aldehyde hydrogenation step when alcohols are a desired product. The production of hydroformylation products having a relatively high normal to branched product isomer ratio is also often exceedingly difficult, if at all possible, in many of the practical scale processes now in use. Another problem in many commonly practiced hydroformylation processes is by-product formation on account of competing reactions. Examples of such unwanted by-products include alkanes, formed through competing olefin hydrogenation, olefin isomers formed through double bond isomerization, ketone formation and aldols generated as a result of product aldehyde condensation reactions.

In commercially practiced hydroformylation processes cobalt and rhodium-catalyzed systems are most commonly used; and while cobalt and rhodium have been the focus of much of the prior hydroformylation research, numerous other metals have been disclosed as catalysts for this synthesis.[1]

[1 For a review of the prior art pertaining to the use of cobalt and rhodium-based hydroformylation processes see: R. L. Pruett, "Advances in Organometallic Chemistry", Vol. 17, page 1 (1979).]

Typical of the prior art relating to the use of ruthenium as a hydroformylation catalyst are the publications of Wilkinson and co-workers. In British Pat. No. 1,138,601, Example 6, the hydroformylation of the alpha-olefins (1-hexane) to aldehydes is described using soluble, phosphine-stabilized ruthenium catalyst precursors, such as $[(Ph_2EtP)_6Ru_2Cl_2]Cl$. Here moderately high pressures are used and the use of a two step hydroformylation and subsequent hydrogenation step as a synthetic route to alcohols is discussed. Additional information regarding the use of a variety of tertiary-phosphine-ruthenium complexes in the catalytic hydroformylation of alkenes to aldehydes-particularly the dependence of conversion and aldehyde ratios upon catalyst concentration, temperature, partial and total pressures, nature of the substrate, and the addition of excess phosphine may be found in a second publication by this group in J. Chem. Soc., page 399 (1976). Similar classes of catalysts are disclosed also in U.S. Pat. No. 3,239,566, assigned to Shell Oil Company. In particular, this patent relates to the production of aldehydes and/or alcohols by the addition of carbon monoxide and hydrogen to olefinic hydrocarbons in the presence of a catalyst consisting of a ruthenium or rhodium component in complex combination with carbon monoxide and a trialkylphosphine. Here, the greatest percentage of the converted olefins form alcohols and aldehydes with less than seven carbons.

Data regarding the application of multidentate phosphine-ruthenium complexes useful in the catalytic hydroformylation of alkenes to alkanes may also be found in the publication of G. Wilkinson et. al. (J. Chem. Soc. Dalton, 1976,399). A variety of multidentate phosphine-platinum complexes useful in catalytic hydroformylation of alkenes to aldehydes are described in U.S. Pat. No. 4,229,381.

The use of ruthenium salts, such as ruthenium(III) chloride and ruthenium stearate, as well as ruthenium carbonyls and ruthenium on carbon, as catalyst precursors, for the hydroformylation of olefins to straight-chain and branched aldehydes is disclosed in British Pat. Nos. 966,461 and 999,461, assigned to Imperial Chemical Industries Limited. Pettit, in U.S. Pat. No. 4,306,084, describes an oxo process reaction where the ruthenium carbonyl catalyst is maintained in a basic solution. Recently the cluster anion, $[HRu_3(CO)_{11}]^-$, has been shown to catalyze the hydroformylation of ethylene and propylene to $C_3$-$C_4$ aldehydes in dimethylformamide at 100° C. (see C. Suss-Fink, J. Organomet. Chem., 193, C20 (1980)).

Polymer-bound ruthenium hydroformylation catalysts, prepared for example by reacting diphenyl-phosphinated styrene-divinylbenzene resins with phosphine-stabilized ruthenium carbonyls, have also been described recently. Pittman, in J. Org. Chem. 46, 1901 (1981), finds improved normal/branched aldehyde ratios with these resins compared with homogeneous catalyst versions. The more desirable alcohol products are not reported to be formed with this class of ruthenium catalyst.

U.S. Pat. No. 3,239,569 discloses the production of aldehydes and alcohols in a single stage conversion which comprises contacting an olefinic hydrocarbon with carbon monoxide and hydrogen in the presence of a catalyst system comprising cobalt in complex combination with carbon monoxide and a trialkylphosphine. Here again, the majority of the hydroformylation products were six carbons or less.

There is then a need in the art for a one stage process for preparing alcohols from olefinically unsaturated compounds by a process which utilizes lower pressures and results in a high yield of predominantly linear alcohols of the $C_3$-$C_{20}$ range.

An object of this invention, therefore, is the oxonation of olefins, particularly higher molecular weight, $C_8$-$C_{20}$ olefin fractions, to produce predominantly aliphatic alcohols from internal olefins at pressures lower than previously used and finally, to outline a method of recovering the product alcohol from non-volatile ruthenium catalyst.

SUMMARY OF THE INVENTION

This invention concerns a method of making alcohols and aldehydes which comprises the steps of contacting a mixture of CO and $H_2$ and terminal or internal olefins with a catalyst system composed of a ruthenium-containing compound and a phosphine-containing promoter, dispersed in a low melting quaternary phosphonium or ammonium base or salt, and heating said resultant reaction mixture under a pressure of 100 psi or greater at a temperature of at least 50° C. for a sufficient time to produce said alcohols and aldehydes.

DETAILED DESCRIPTION OF THE INVENTION

In the narrower and more preferred practice of this invention, alcohols and aldehydes are prepared concurrently from a synthesis gas mixture of carbon monoxide, hydrogen and olefin substrates by a process comprising:

(a) Contacting said mixture of carbon monoxide, hydrogen and terminal and/or internal olefin with a catalyst system composed of a ruthenium-containing compound in conjunction with a phosphine-containing promoter dispersed in a low melting quaternary phosphonium salt of an organic or mineral acid.

(b) Heating said reaction mixture to a temperature of between 100° to 220° C., at a pressure of 500 psi or greater, and (c) Isolating said alcohols contained therein.

In order to present the inventive concept in the greatest possible detail to promote its understand, the following supplementary disclosure is submitted. The basic invention, improved upon here is practiced as follows:

Catalysts that are suitable in the practice of this invention contain ruthenium. The ruthenium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise ruthenium and phosphine in complex combination with carbon monoxide, hydrogen and possibly one or more olefin substrates. The most effective catalyst is believed to be achieved where a ruthenium species in conjunction with a multidentate phosphine promoter is solubilized in a quaternary salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium (III) chloride hydrate, ruthenium(III) bromide, ruthenium(III) triiodide, tricarbonyl ruthenium(II) iodide, anhydrous ruthenium (III) chloride and ruthenium nitrate, or as the salt of a suitable organic carboxylic acid, for example, ruthenium(III) acetate ruthenium naphthenate, and ruthenium valerate. Ruthenium(III) acetylacetonate is also a suitable catalyst precursor. The ruthenium may furthermore be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of a mineral acid, ruthenium salts of an organic carboxylic acid and ruthenium carbonyl or hydrocarbonyl derivatives. Among the particularly preferred are ruthenium(IV) dioxide, ruthenium(III) acetylacetonate, and triruthenium dodecacarbonyl. The usefulness of these ruthenium precursors for alcohol and aldehyde synthesis is illustrated by the accompanying Examples I-XX.

The ruthenium-containing compound is, prior to its catalytic use in making alcohols and aldehydes, first dispersed in a low melting quaternary phosphonium salt. It is interesting to note that the ruthenium-containing compound alone, without being dispersed in said salt, produces lower yields of alkanols. Alkanes, resulting from the hydrogenation of the olefin, are the major product (Example XXI).

The quaternary phosphonium salt must be relatively low melting, that is, melt at a temperature less than about the temperature of reaction of making alcohols. Usually the quaternary compound has a melting point less than about 180° C., and most often has a melting point less than 150° C.

Suitable quaternary phosphonium salts have the formula:

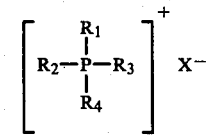

where $R_1$, $R_2$, $R_3$ and $R_4$ are organic radicals, particularly alkyl, aryl or alkaryl radicals bonded to the phosphorous atom, and X is an anionic species. The organic radicals particularly useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commerical production. The corresponding quaternary phosphonium acetates, hydroxides, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium iodide, tetrabutylphosphonium chloride, hexadecyl tributylphosponium bromide, tetrabutylphosphonium nitrate, tetrabutylphosphonium chromate, tetrabutylphosphonium tetrafluoroborate and tetrabutylphosphonium acetate. Tables I-III provide evidence of the effectiveness of these quaternary phosphonium salts when in combination with ruthenium(IV) oxide, triruthenium dodecacarbonyl and ruthenium(II) acetylacetonate.

The preferred quaternary salts are generally the tetralkylphosphonium salts containing alkyl groups having 1-6 carbon atoms, such as methyl, ethyl and butyl. Preferred tetrabutylphosphonium salts include the bromide, chloride, iodide, acetate and chromate salts. Tetrabutyl-phosphonium salts such as tetrabutylphosphonium bromide are most preferred for the practice of this invention.

Mixed alkyl quaternary salts containing two or more different alkyl groups, each containing 1-20 carbon atoms, such as methyl, ethyl, butyl, decyl, dodecyl, hexadecyl, are also preferred. These alkyl quaternary salts may be added as their bromide, chloride, iodide, acetate and chromate salts. Preferred mixed alkyl quaternary salts include hexadecyltributylphosphonium bromide.

Phosphine promoters are generally added in the practice of this invention for the purpose of improving the product alcohol or aldehyde linearity (e.g. the ratio of straight-chain aliphatic alcohol product (A), to branched-chain alcohol product illustrated in Equation 2 by structure B).

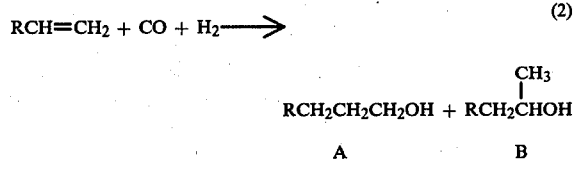

$$RCH=CH_2 + CO + H_2 \longrightarrow \quad (2)$$

$$RCH_2CH_2CH_2OH + RCH_2\overset{CH_3}{\underset{|}{C}}HOH$$

$$\quad A \qquad\qquad\qquad B$$

Suitable promoters contain one or more trivalent phosphorus atoms per molecule, each bonded to one or more carbon atoms. These phosphines may be diphosphines, containing two phosphorus atoms per molecule, polyphosphines or monophosphines. The trivalent phosphorus atoms in the diphosphine and polyphosphine molecules may be separated by 0 to 12 carbon atoms, or bonded to different cyclopentadienyl or arene groups of a metallocene. Phosphine promoters of the bidentate and multidentate type include, but are not limited to, bis(1,3-diphenylphosphino)propane, bis(1,2-diphenylphosphino)ethane, bis(1,4-diphenylphosphino)butane, bis(1,5-diphenylphosphino)pentane, bis(1,6-diphenylphosphino) hexane, bis(1,1-diphenylphosphino)-methane, tris(2-diphenylphosphinoethyl)-phosphine,1,1,1-tris(diphenylphosphinomethyl)ethane, 1,1'-bis(diphenylphosphino) ferrocene and bis(2-diphenylphosphinoethyl)phenyl phosphine.

Monodentate phosphines such as triphenylphosphine and tributylphosphine may also be used, but are generally not as desirable. Substituted promoters, such as tri(2-cyanoethyl)phosphine, are also effective in the application of this ruthenium-catalyzed hydroformylation reaction.

The olefins employed in the practice of this invention include internal and terminal olefins containing two to thirty carbon atoms and mixtures of the same. Examples of suitable olefins include straight-chain terminal olefins such as propylene, 1-butene, 1-octene, 1-decene, 1-dodecene, 1-tetradecene, and 1-hexadecene. Also suitable are branched-chain, terminal olefins such as 3-methyl-1-pentene, 4-methyl-1-hexene, 3,3-dimethyl-1-butene and 3,4-dimethyl-1-hexene. Linear and branched, internal olefins are also suitable substrates for this hydroformylation. Examples include 2-octene, 3-octene, 4-octene, mixed internal octenes, mixed internal decenes, mixed internal dodecenes; as well as 2-pentene, 3-hexene, 5-decene, 2-decene, 2-dodecene, and 5-methyl-2-hexene. Cyclic olefins like cyclohexane, cyclopentene, cycloheptene and their branched derivatives such as 1-methylcyclohexene and 2-ethylcyclopentene are also useful in the practice of this invention.

Particularly preferred are straight-chain terminal olefins such as propylene, 1-butene, 1-octene, 1-decene and 1-dodecene, as well as linear internal olefins such as 2-octene, mixed internal octenes, mixed internal undecenes and mixed internal $C_{13}$-$C_{14}$ olefins, as well as terminal, internal olefin mixtures thereof.

The quantity of ruthenium catalyst (exclusive of quaternary salt) employed in the instant invention is not critical and may vary over a wide range. In general, the improved process is desirably conducted in the presence of a catalytically effective quantity of the active ruthenium species, phosphine promoter and quaternary phosphonium salt which gives the desired products in reasonable yields. The reaction proceeds when employing as little as about $1 \times 10^{-6}$ weight percent, and even lesser amounts, of ruthenium together with about $1 \times 10^{-6}$ weight percent of phosphine promoter and $1 \times 10^{-6}$ weight percent of quaternary phosphonium salt, basis the total weight of the reaction mixture. The upper concentration is dictated by a variety of factors including catalyst cost, partial pressures of carbon monoxide and hydrogen, operating temperature etc. A ruthenium catalyst concentration of from about $1 \times 10^{-5}$ to about 30 weight percent ruthenium in conjunction with a phosphine promoter concentration of $1 \times 10^{-5}$ to about 30 weight percent and a low melting quaternary phosphonium salt concentration of from about 0.1 to about 80 weight percent based on the total weight of reaction mixture is generally desirable in the practice of this invention. The preferred ruthenium to low melting quaternary phosphonium salt atomic ratio is from about 0.01 to about 10.

The temperature range which can usefully be employed in these syntheses is a variable dependent upon other experimental factors, including the pressure, the concentration and the choice of the particular species of ruthenium catalyst among other things. The range of operability is from about 50° to 350° C. when superatmospheric pressures of syngas are employed. A narrow range of 100°-220° C. represents the preferred temperature range.

Superatmospheric pressures of 100 psi or greater lead to substantial yields of alcohols by the process of this invention. A preferred operating range is above 500 psi, pressures above 3000 psi also provide useful yields of desired alcohol.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may or may not undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The major by-products of these alcohol and aldehyde syntheses are most commonly alkanes, isomerized olefins, and aldols, which are, of course, also useful compounds and major articles of commerce. The aldehydes and alcohols can easily be separated from one another by conventional means, eg. fractional distillation in vacuo.

The aldehyde and alcohol products may be readily separated from the ruthenium-catalyst-containing crude product mixture by conventional means, eg., by fractional distillation in vacuo. The by-products identifed supra may also be isolated by conventional means, or they may be recycled with the ruthenium catalyst.

The novel process of this invention can be conducted in a batch, semi-continuous or continuous fashion. The catalyst may be initally introduced into the reaction zone batchwise, or it may be continuously or intermittently introduced into such a zone during the course of the synthesis reaction. Operating conditions can be adjusted to optimize the formation of the desired alcohol product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Having described the inventive process, the following examples are submitted to supply specific and illustrative embodiments:

The synthesis of predominantly linear $C_9$ alcohols from 1-octene via ruthenium melt catalysis wherein the catalyst precursor is ruthenium(IV) oxide plus bis(1,3-diphenylphosphino) propane dispersed in tetrabutylphosphonium bromide (mp. 100° C.), is demonstrated in Example I.

EXAMPLE I

Ruthenium(IV) oxide hydrate (1.146 g, 6.0 mmole) plus bis(1,3-diphenylphosphino)propane (2.475 g, 6.0 mmole) was dispersed in tetrabutylphosphonium bromide (10.0 g, 29.5 mmole), diluted with 1-octene (22.4 g, 200 mmole) and transferred in a glass liner, under $N_2$ purge, to an 850 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for four hours and then allowed to cool.

Upon reaching ambient temperature, the reactor pressure (1000 psi) was noted, a typical gas sample taken, and the excess gas removed. The deep-red liquid product (39.5 g) was analyzed by GLC and Karl Fischer titration.

Analysis of a typical liquid sample showed the following composition:
- 42.4 wt. % 1-nonanol
- 8.0 wt. % branched C-9 alcohols
- 1.0 wt. % C-9 aldehydes
- 1.2 wt. % water
- 17.4 wt. % n-octane
- 28.2 wt. % unreacted octenes Analysis of typical gas samples showed the presence of:
- 68 wt. % Hydrogen
- 32 wt. % Carbon monoxide
- 20 wt. % Carbon dioxide Estimated linearity of the nonanol fraction is 84%.
Estimated conversion of octent charge=68%.
Estimated total yield of nonanols (basis octene converted) is 67 mole%.

EXAMPLE II

Triruthenium dodecacarbonyl (1.78 g, 2.0 mmole) plus bis(1,3-diphenylphosphino)propane (2.478 g, 6.0 mmole) was dispersed in tetrabutylphosphonium bromide (10.0 g, 29.5 mmole) and diluted with 1-octene (22.4 g, 200 mmole) and transferred in a glass liner, under $N_2$ purge, to an 850 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for four hours and then allowed to cool.

Upon reaching ambient temperature, the reactor pressure (1050 psi) was noted, a typical gas sample taken, and the excess gas removed. The deep-red liquid product (38.7 g) was analyzed by glc and Karl Fischer titration.

Analysis of a typical liquid sample showed the following composition.
- 30.4 wt.% linear nonanols
- 8.4 wt.% branched nonanols
- 18.4 wt.% octenes
- 38.9 wt.% octane
- 1.3 wt.% nonanals Estimated linearity of the nonanol fraction is 78%.
Estimated conversion of octene charge is 80%.
Estimated total yield of nonanols basis octene converted is 42%.

EXAMPLE III

In this example the same olefin feed were used as in Example I and II, however, ruthenium acetylacetonate (2.390 g, 6.0 mmole) was the ruthenium compound bis(1,3-diphenylphosphino)propane (2.475 g, 6.0 mmole) was the phosphine promoter, and the catalyst precursors were dispersed in $C_{16}H_{33}Bu_3PBr$ (10.0 g, 29.5 mmole). As with Examples I and II the mixture was transferred in a glass liner, under $N_2$ purge, to an 850 ml capacity pressure reactor equipped with heating and means of agitation. The reactor was sealed, flushed with $CO/H_2$ and pressured to 1200 psi with $CO/H_2$ (1:2). The mixture was heated to 180° C. with rocking, held at temperature for four hours and then allowed to cool.

Upon reaching ambient temperature, the reactor pressure (1200 psi) was noted, a typical gas sample taken, and the excess gas removed. The deep-red liquid product (41.6 g) was analyzed by GLC and Karl Fischer titration.

Analysis of a typical liquid sample showed the following composition:

28.6 wt.% linear nonanols
6.9 wt.% branced nonanols
5.3 wt.% octenes
46.1 wt.% octane
0.7 wt.% nonanals
Estimated linearity of the nonanol fraction is 81%.
Estimated conversion of octene charge is 94%.
Estimated total yield of nonanols basis octene converted is 35%.

EXAMPLE IV-XI

In the following table, Table I data are summarized for Examples IV-XI in which the ruthenium-containing compound is ruthenium(IV) oxide hydrate (6.0 mmole), the quaternary salt is tetra-n-butylphosphonium bromide (10.0 g, 29.5 mmole) and the olefin is 1-octene (22.4 g, 200 mmole). These runs were completed in the same manner as Examples I–III. However, in these runs different di- and poly-phosphine promoters were used. It may be noted that:

(a) The $RuO_2$—$PH_2PCH_2CH_2CH_2PPh_2$ and $RuO_2$—$CH_3$—$C(CH_2PPh_2)_3$ catalyst precursors generated nonanol product with as high as 84% linearity.

(b) The total yield of nonanol product in Example 4, with the $RuO_2$—$Ph_2PCH_2CH_2PPh_2$ combination, is 84 mole %.

(c) The $RuO_2$—$Ph_2PCH_2PPh_2$ catalyst precursor in Example 10 gives nonanol product with 87% linearity.

TABLE I

OXO ALCOHOLS FROM TERMINAL OLEFINS

| | | Liquid Product Composition (%) | | | | |
|---|---|---|---|---|---|---|
| | | Unreacted | | | Nonanols | Nonanol |
| Example | Promoter | Octenes | Octane | Nonanals | Branched Linear | Linearity |
| 4 | $Ph_2PCH_2CH_2PPh_2$ | 30.1 | 10.8 | 2.4 | 11.2 40.9 | 79 |
| 5 | $Ph_2PCH_2CH_2CH_2PPh_2$ | 28.2 | 17.4 | 1.0 | 8.0 42.4 | 84 |
| 6 | $(Ph_2PCH_2CH_2)_2$ | 19.0 | 10.5 | 6.9 | 19.3 38.0 | 66 |
| 7 | $CH_3$—$C(CH_2PPh_2)_3$ | 61.7 | 6.7 | 1.9 | 4.2 22.0 | 84 |
| 8 | $P(CH_2CH_2PPh_2)_3$ | 36.2 | 10.9 | 0.8 | 8.7 38.2 | 81 |
| 9 | $(Ph_2PC_5H_4)_2Fe$ | 26.8 | 6.1 | 8.6 | 8.0 29.4 | 79 |
| 10 | $Ph_2PCH_2PPh_2$ | 36.9 | 16.6 | 6.9 | 4.6 29.9 | 87 |
| 11 | $Ph_2P(CH_2)_5PPh_2$ | 13.9 | 9.8 | 6.6 | 21.6 38.1 | 64 |

[a]Reaction charge: Ru, 6.0 mmole; Ru: P (as phosphine) = 1:2; Bu$_4$PBr, 29.5 mmole; 1-octene, 200 mmole
Run Conditions: 180° C. 1200 psi of CO/H$_2$ (1:2) initial pressure: 4 hours.

COMPARATIVE EXAMPLES XII AND XIII

The two examples in Table II were conducted in the same manner in all espects as Examples IV–XI, except the phosphine promoters used were monodentate phosphines. (e.g. PPh$_3$ and PBu$_3$). It may be noted that in these examples, the nonyl alcohol linearity is Ca. 60%, considerably below the figures in Table I for ruthenium coupled with diphosphines, polyphosphines and phosphine substituted metallocenes. The data can be summarized as follows:

TABLE II

OXO ALCOHOLS FROM TERMINAL OLEFINS[A]

| | | Liquid Product Composition (%) | | | | | |
|---|---|---|---|---|---|---|---|
| Example | Promoter | Octenes | Octane | Nonanals | Branched | Linear | Linearity |
| 12 | PPh$_3$ | 1.9 | 16.2 | 0.1 | 30.4 | 45.2 | 60 |
| 13 | PBu$_3$ | 4.3 | 14.9 | 0.7 | 27.5 | 42.1 | 60 |

[A]Reaction charge: Ru, 6.0 mmole; Ru: PR$_3$, - 1:2; Bu$_4$PBr, 29.5 mmole; 1-octene, 200 mmole
Run conditions: 180° C. 1200 psi of CO/H$_2$ (1:2) initial pressure; 4 hours.

EXAMPLE XIV-XIX

The method used in Examples 14–19 was the same as that used in Example I, except mixed internal octenes were employed as the typical internal olefin feed stock. Table III, which follows, records the preparation of predominantly linear nonyl alcohols from CO/H$_2$ plus mixed internal olefin fractions, particularly mixed C$_8$-olefin feedstocks, using ruthenium (IV) oxide, hydrated, in combination with certain diphosphine and polyphosphine promoters plus tetra-n-butylphosphonium bromide.

TABLE III

OXO ALCOHOLS FROM INTERNAL OLEFINS[a]

| EXAMPLE | RUTHENIUM PRECURSOR | PROMOTER | QUATERNARY SALT | LIQUID PRODUCT COMPOSITION (%) | | | | | PROPORTION[b] OF PRODUCT |
|---|---|---|---|---|---|---|---|---|---|
| | | | | OCTENES | OCTANE | NONANALS | NONANOLS BRANCHED | LINEAR | |
| 14 | RuO$_2$xH$_2$O | Ph$_2$PCH$_2$CH$_2$PPh$_2$ | Bu$_4$PBr | 92.7 | 5.0 | 0.9 | 0.4 | 0.3 | 40 |
| | | | | [b]50.1 | 2.5 | 4.5 | 14.7 | 16.2 | 60 |
| 15 | RuO$_2$xH$_2$O | Ph$_2$PCH$_2$CH$_2$CH$_2$PPh$_2$ | Bu$_4$PBr | 92.3 | 5.6 | 0.7 | 0.7 | 0.3 | 35 |
| | | | | [b]49.5 | 2.7 | 3.2 | 21.2 | 16.5 | 65 |
| 16 | RuO$_2$xH$_2$O | (Ph$_2$PCH$_2$CH$_2$)$_2$ | Bu$_4$PBr | 87.9 | 6.2 | 3.6 | 0.8 | 0.6 | 16 |
| | | | | [b]55.4 | 3.7 | 7.3 | 16.8 | 14.2 | 84 |

TABLE III-continued
OXO ALCOHOLS FROM INTERNAL OLEFINS[a]

| EX-AM-PLE | RUTHEN-IUM PRECURSOR | PROMOTER | QUATER-NARY SALT | LIQUID PRODUCT COMPOSITION (%) | | | | | PROPORTION[b] OF PRODUCT |
|---|---|---|---|---|---|---|---|---|---|
| | | | | OC-TENES | OC-TANE | NON-ANALS | NONANOLS | | |
| | | | | | | | BRANCHED | LINEAR | |
| 17 | $RuO_2xH_2O$ | $(Ph_2PC_5H_4)_2Fe$[c] | $Bu_4PBr$ | 95.5 | 2.2 | 0.3 | 0.3 | 0.1 | |
| | | | | [b]51.3 | 3.2 | 1.8 | 14.2 | 23.8 | |
| 18 | $RuO_2xH_2O$ | $CH_3C(CH_2PPh_2)_3$[d] | $Bu_4PBr$ | 89.1 | 5.0 | 4.4 | 0.6 | 0.6 | 16 |
| | | | | [b]48.1 | 2.9 | 10.6 | 13.3 | 16.4 | 84 |
| 19 | $RuO_2xH_2O$ | $P(CH_2CH_2CN)_3$[d] | $Bu_4PBr$ | 1.1 | 11.4 | 0.6 | 46.6 | 31.0 | |

[a]Reaction Charge: Ru, 6.0 mmole; Ru: P, 1:2; Bu$_4$PBr, 58.9 mmole; mixed internal octenes, 200 mmole.
Run Conditions: 180° C.; 1200 psi CO/H$_2$ (1:2) initial pressure, 4 hours.
[b]Two-phase liquid product.
[c]Reaction charge, Ru, 3.0 mmole; Ru: P, 1:2; Bu$_4$PBr, 29.5 mmole; mixed internal octenes, 100 mmole.
[d]Reaction Charge: Ru, 1.5 mmole; Ru: P, 1.5:1; Bu$_4$PBr, 29.5 mmole; mixed internal octenes, 100 mmole.

EXAMPLE XX

Ruthenium(IV) oxide hydrate (0.573 g, 3.0 mmole) plus bis(2-diphenylphosphinoethyl)phenylphosphine (1.604 g 3.0 mmole) was dispersed in tetrabutylphosphonium bromide (5.0 g, 14.7 mmole), diluted with mixed internal octenes (11.22 g, 100 mmole) and transferred in a glass liner, under N$_2$ purge, to the 850 ml capacity pressured reactor of Example I. The reactor was sealed, flushed with CO/H$_2$ and pressured to 1200 psi and CO/H$_2$ (1:2). The mixture was heated to 180° C. with rocking, held at temperature for four hours and then allowed to cool.

Analysis of the two-phase liquid product composition (18.3 g) was as follows:

| | % Composition | |
|---|---|---|
| | 1$^{st}$ Phase | 2$^{nd}$ Phase |
| Octene | 91.9 wt. % | 43.3 wt. % |
| Octane | 2.8 wt. % | 1.7 wt. % |
| Linear Nonanal | 1.0 wt. % | 4.7 wt. % |
| Branched Nonanal | 0.3 wt. % | 0.7 wt. % |
| Linear Nonanol | 1.9 wt. % | 37.5 wt. % |
| Branched Nonanol | 0.1 wt. % | 2.2 wt. % |
| Water | 0.1 wt. % | 2.7 wt. % |

Estimated lineartiy of the nonanol fraction is 94%.

COMPARATIVE EXAMPLE XXI

This example shows the poorer performance for the ruthenium catalyst in the absence of a quaternary phosphonium salt and phosphine promoter.

A mixture of ruthenium(IV) oxide, hydrate (1.1469) 6.0 mmole) and 1-octene (22.4 g, 200 mmole) was transferred in a glass liner under N$_2$ purge, to an 850 ml capacity pressure reactor equipped with heating and means of agitation. As in Example I, the reactor was sealed, flushed with CO/H$_2$ and pressured to 1200 psi with CO/H$_2$ (1:2). The mixture was heated to 180° C. with rocking, held at temperature for 4 hours, and then allowed to cool.

Upon reaching ambient temperature, the reactor was depressured, and the two-phase liquid product (40.1 g, 45 ml) was analyzed by glc and Karl Fischer Titration. The bottom phase (10 ml) proved to be water. Analysis of the top phase (35 ml) shows the following composition.

13.0% 1-nonanol
7.8% Branched C-9 alcohols
1.9% C-9 aldehydes
33.5% n-octane
6.5% unreacted octenes Estimated linearity of the nonanol fraction is 63%.

Estimated conversion of octene charge=91%.
Estimated total yield of C$_9$-alcohols (basis octene converted) is 24 mole%.

In comparing these results with those of Example I it may be noted that:

(a) The estimated total yield of C$_9$-alcohol product is higher in Examples I (67 mole%), with added quaternary salt plus phosphine promoter than in this comparative Example.

(b) The production of by-product hydrocarbon, in this case octane, is lower in Example 1, with the added tetrabutylphosphonium bromide plus phosphine promoter, than in the Example 21 (e.g. 17.4 wt% octane versus 33.5 wt% in this Example).

(c) The linearity of the nonanol product fraction is higher in Example I (84%), versus 63% for Example 21, where the ruthenium catalyst is without phosphine promoter plus quaternary phosphonium salt.

What is claimed:

1. An oxo process for preparing alcohols and aldehydes, particularly aliphatic alcohols which comprises the steps of contacting a variety of C$_2$–C$_{30}$ terminal and internal olefins plus synthesis gas with a catalyst system comprising a ruthenium-containing compound derivative in conjunction with one or more bidentate or multidentate phosphine promoters dispersed in a low-melting quaternary phosphinium salt, and heating the resultant reaction mixture under a pressure of 100 psi or greater at a temperature of at least 50° C.

2. The process of claim 1 wherein said olefins are alpha olefins.

3. The process of claim 2 wherein said olefin is 1-octene.

4. The process of claim 1 wherein said olefin is a mixed internal olefin.

5. The process of claim 1 wherein the ratio of CO:H$_2$ in the synthesis gas mixture is from 20:1 to 1:20.

6. The process of claim 1 wherein said ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

7. The process of claim 6 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecacarbonyl.

8. The process of claim 7 wherein said ruthenium-containing compound is selected from the group consisting of ruthenium(IV) dioxide, triruthenium dodecacarbonyl and ruthenium(III) acetylacetonate.

9. The process of claim 8 wherein said ruthenium-containing compound is ruthenium oxide.

10. The process of claim 1 wherein said quaternary salt has a melting point less than 180° C.

11. The process of claim 1 wherein said quaternary salt is a tetraalkylphosphonium salt.

12. The process of claim 11 wherein said alkyl groups contain 1–20 carbon atoms.

13. The process of claim 12 wherein said tetraalkylphosphonium salt is a tetrabutylphosphonium salt.

14. The process of claim 13 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

15. The process of claim 1 wherein said quaternary salt is a mixed alkylphosphonium salt.

16. The process of claim 15 wherein said alkyl groups contain 1–20 carbon atoms.

17. The process of claim 16 wherein said mixed alkylphosphonium salt is a hexadecyltributylphosphonium salt.

18. The process of claim 17 wherein said hexadecyltributylphosphonium salt is selected from the group consisting of hexadecyltributylphosphonium bromide, hexadecyltributylphosphonium chloride, hexadecyltributylphosphonium iodide, hexadecyltributylphosphonium acetate, and hexadecyltributylphosphonium chromate.

19. The process of claim 1 wherein said phosphine promoter contains two or more trivalent phosphorus atoms per molecule.

20. The process of claim 19 wherein said phosphine is selected from the group consisting of bis(1,2-diphenylphosphino)ethane, bis(1,1-diphenylphosphino)methane, bis(1,3-diphenylphosphino)propane, bis(1,5-diphenylphosphino)pentane, 1,1'-bis(diphenylphosphino)ferrocene, bis(1,4-diphenylphosphino)butane, tris(2-diphenylphosphinoethyl)phosphine, 1,1,1-tris(diphenylphosphinomethyl)ethane, and bis(2-diphenylphosphinoethyl)phenylphosphine.

21. The process of claim 1 wherein said temperature range is from about 100° C. to about 220° C.

22. The process of claim 1 wherein said pressure is from about 500 psi to about 3000 psi.

23. The process of claim 1 wherein said alpha olefin is 1-octene, said ruthenium-containing compound is ruthenium(IV) oxide, said phosphine promoter is a multidentate phosphine promoter and said quaternary phosphonium salt is tetra-n-butylphosphonium bromide.

* * * * *